(12) United States Patent
Kim et al.

(10) Patent No.: US 10,835,459 B2
(45) Date of Patent: Nov. 17, 2020

(54) THREE-DIMENSIONAL MOLDING TYPE POWDER MAKEUP COSMETIC COMPOSITION

(71) Applicant: COSON CO., LTD., Seoul (KR)

(72) Inventors: Young Ju Kim, Yongin-si (KR); Chan Gi Lee, Yongin-si (KR)

(73) Assignee: COSON CO., LTD, Seoul (KR)

( * ) Notice: Subject to any disclaimer, the term of this patent is extended or adjusted under 35 U.S.C. 154(b) by 17 days.

(21) Appl. No.: 16/324,522

(22) PCT Filed: Aug. 2, 2017

(86) PCT No.: PCT/KR2017/008361
§ 371 (c)(1),
(2) Date: Feb. 8, 2019

(87) PCT Pub. No.: WO2018/030706
PCT Pub. Date: Feb. 15, 2018

(65) Prior Publication Data
US 2019/0175457 A1   Jun. 13, 2019

(30) Foreign Application Priority Data

Aug. 9, 2016   (KR) ........................ 10-2016-0101481

(51) Int. Cl.
| | | |
|---|---|---|
| *A61K 8/04* | (2006.01) |
| *A61K 8/06* | (2006.01) |
| *A61K 8/02* | (2006.01) |
| *A61K 8/92* | (2006.01) |
| *A61Q 19/00* | (2006.01) |
| *A61Q 1/00* | (2006.01) |
| *A61Q 1/12* | (2006.01) |
| *A61K 8/891* | (2006.01) |
| *A61K 8/73* | (2006.01) |
| *A61K 8/58* | (2006.01) |
| *A61K 8/34* | (2006.01) |
| *A61K 8/44* | (2006.01) |
| *A61K 8/31* | (2006.01) |
| *A61K 8/892* | (2006.01) |
| *A61Q 1/02* | (2006.01) |
| *A61K 8/37* | (2006.01) |
| *A61K 8/42* | (2006.01) |
| *A61K 8/81* | (2006.01) |
| *A61Q 1/10* | (2006.01) |
| *A61Q 1/06* | (2006.01) |
| *A61Q 1/08* | (2006.01) |

(52) U.S. Cl.
CPC ................ *A61K 8/04* (2013.01); *A61K 8/022* (2013.01); *A61K 8/31* (2013.01); *A61K 8/342* (2013.01); *A61K 8/37* (2013.01); *A61K 8/42* (2013.01); *A61K 8/442* (2013.01); *A61K 8/585* (2013.01); *A61K 8/73* (2013.01); *A61K 8/732* (2013.01); *A61K 8/8111* (2013.01); *A61K 8/891* (2013.01); *A61K 8/892* (2013.01); *A61K 8/92* (2013.01); *A61Q 1/00* (2013.01); *A61Q 1/02* (2013.01); *A61Q 1/12* (2013.01); *A61Q 19/00* (2013.01); *A61Q 1/06* (2013.01); *A61Q 1/08* (2013.01); *A61Q 1/10* (2013.01)

(58) Field of Classification Search
CPC .. A61K 2300/00; A61K 8/042; A61K 9/0014; A61K 47/44; A61K 8/04; A61K 8/022; A61Q 19/00; A61Q 1/00; A61Q 1/12
See application file for complete search history.

(56) References Cited

U.S. PATENT DOCUMENTS 5,266,321 A * 11/1993 Shukuzaki ............. A61K 8/375
424/401
6,348,479 B1 * 2/2002 Mori ........................ A61K 8/06
514/357

FOREIGN PATENT DOCUMENTS

| JP | 2005-247808 A | 9/2005 |
| JP | 2015-214506 A | 12/2015 |
| KR | 10-2016-0040791 A | 4/2016 |
| KR | 10-1727027 B1 | 4/2017 |

* cited by examiner

*Primary Examiner* — Tracy Liu
(74) *Attorney, Agent, or Firm* — Heedong Chae; Lucem, PC

(57) ABSTRACT

The present invention relates to a three-dimensional molding type powder makeup cosmetic composition, wherein the powder makeup cosmetic composition has a soft feeling of use and excellent adhesion and sustain power and mitigates the generation of creases by containing a powder phase in an oil gel phase and the powder makeup cosmetic composition can be molded into various three-dimensional designs due to physical characteristics of the oil gel phase.

2 Claims, No Drawings

THREE-DIMENSIONAL MOLDING TYPE POWDER MAKEUP COSMETIC COMPOSITION

CROSS-REFERENCE TO RELATED APPLICATIONS

This application is based on and claims the benefit of priority to Korean Patent Application No. 10-2016-0101481 filed on Aug. 9, 2016, with the Korean Intellectual Property Office, the disclosure of which is incorporated herein by reference.

TECHNICAL FIELD

The present invention relates to a three-dimensional molding type powder makeup cosmetic composition, wherein the powder makeup cosmetic composition has a soft feeling of use and excellent adhesion and sustain power and mitigates the generation of creases by containing a powder phase in an oil gel phase and the powder makeup cosmetic composition can be molded into various three-dimensional designs due to physical characteristics of the oil gel phase.

BACKGROUND ART

In general, a compressed powder makeup cosmetic composition may be classified, according to used raw materials, into a powder type obtained by mixing an oil binder with powder and a compressed powder type obtained by compressing only the powder.

According to the manufacturing and molding method, the compressed powder makeup cosmetic composition may be classified into a baked type in which the powder mixed and agitated with an oil-water phase emulsion or water phase is molded and dried, an injection type in which a solvent is mixed with a powder slurry to form sludge and the sludge is injected into a molding container and dried, and a jelly type in which a powder is mixed with a high-content elastomer gel or wax binder and molded.

Among the makeup cosmetic compositions, the powder type contains an oil binder to increase the cohesiveness of the powder and prevent a breakage against an external impact. However, dusting is severe and the skin adhesion and the sustain power are remarkably decreased. In addition, since the content of pearl mixed with the makeup cosmetic composition is low, the luster of the pearl is decreased. To eliminate the above disadvantages of the powder type, the research and development for modifying a surface of a pigment to improve the skin adhesion and the dusting, and there has been studies on a cosmetic composition capable of containing the high-content of pearl.

The baked type and the injection type are used to contain the high-content of pearl. The baked type and the injection type has the soft feeling of use, increases the skin adhesion of pearl having a large particle size, and implements a three-dimensional molding by overcoming the limitation of a planar press type powder cosmetic composition. However, the baked type has the matt feeling of use and the low sustain power. Although the injection type has the improved glossiness of pearl and the sustain power of cosmetics, the stability of formulation is lowered when the high-content pearl is mixed.

Although the jelly type cosmetic composition recently has been developed to stably contain the high-content pearl and improve the color formation and the sustain power, the jelly type cosmetic composition is molded only in a dome shape, and cannot be molded into various three-dimensional designs. In addition, as for an aspect of the composition, because the composition is deformed in one direction upon impact, there is a limit to the molding stability and thus a distribution is not smoothly performed. In addition, a crease phenomenon easily occurs because excessive oil binders are contained.

In general, the powder cosmetic composition is mainly used for a product which is expressed by using embossed or engraved patterns or letters with a two-dimensional planar design.

The powder cosmetic composition having the two-dimensional planar design has reached the limit to meet not only use as a makeup cosmetic composition but also aesthetic desires, with respect to consumers who are interested in beauty.

The formulation for improving the spreadability and improving the unique feeling of use has been researched and developed in the related art, and studies for modifying powder surfaces or developing powder binders have been conducted to improve the dusting, skin adhesion and durability.

Recently, regarding the powder cosmetic composition, studies have been conducted in the development of powder for increasing skin gloss, the adjustment of the powder particle size and shape for improving light reflection efficiency, the powder synthesis technology, and so on. Studies have been continuing to overcome the limitations of molding the conventional powder cosmetic composition, including various three-dimensional molding in addition to the plane compression molding.

Accordingly, it is required to develop a powder makeup cosmetic composition, which has the soft feeling of use and the excellent adhesion, has excellent durability and color formation, mitigates the crease phenomenon, and has a three-dimensional shape.

DISCLOSURE

Technical Problem

Thus, studies have been conducted repeatedly in order to solve the above problems, the three-dimensional molding type powder makeup cosmetic composition has been developed by containing a powder phase in an oil-gel phase, thereby having the soft feeling of use, and excellent skin adhesion and sustain power, removing the crease phenomenon, and improving the moldability, and thus the present invention has been completed.

The present invention provides a makeup cosmetic composition for having the soft feeling of use and excellent adhesion and sustain power, and mitigating the generation of creases, by containing a powder phase in an oil-gel phase.

In addition, the present invention provides a makeup cosmetic composition improved in the moldability due to the physical properties in which the oil-gel phase is phase-transformed at a predetermined temperature.

Technical Solution

To this end, the present invention provides a three-dimensional molding type powder makeup cosmetic composition improved in the moldability by containing a powder phase in an oil-gel phase.

In addition, the oil-gel phase gelates by mixing oil with a gelling agent.

In addition, the powder phase includes an inorganic pigment, an organic pigment, pearl powder and an extender pigment.

Advantageous Effects

The present invention can provide a three-dimensional molding type powder makeup cosmetic composition containing a powder phase in an oil-gel phase In addition, the present invention can provide a three-dimensional molding type powder makeup cosmetic composition having the soft feeling of use, and excellent adhesion and sustain power, and mitigating the generation of creases.

In addition, the present invention can provide a three-dimensional molding type powder makeup cosmetic composition improved in the moldability.

DESCRIPTION OF DRAWINGS

Best Mode

Mode for Invention

According to the present invention, the three-dimensional molding type powder makeup cosmetic composition has been developed, and it was confirmed that a powder phase is contained in an oil-gel phase, so that the three-dimensional molding type powder makeup cosmetic composition has the soft feeling of use, excellent adhesion and sustain power, effectively mitigates the crease, and has improved glossiness and color formation of pearl when applied on a skin.

In addition, according to the present invention, it was confirmed that the physical properties was used in which the oil-gel phase is phase-transformed at a predetermined temperature, so that the three-dimensional molding type powder makeup cosmetic composition of the present invention could be molded into various three-dimensional ways, and the pay-off and molding stability (dropping stability and high-temperature stability) were excellent in Examples and Test examples.

Hereinafter, the present invention will be described in detail.

The three-dimensional molding type powder makeup cosmetic composition of the present invention is composed of an oil-gel phase and a powder phase.

The powder makeup cosmetic composition has a hardness of 4.0 kg/cm² to 40 kg/cm², and preferably from 5.0 kg/cm² to kg/cm². The hardness is an important factor, which affects the feeling of use (spreadability, dispersion, etc.) and the molding stability of the powder makeup cosmetic composition, and determines an amount of pay-off of the powder makeup cosmetic composition. In addition, when applied onto the skin, the hardness affects the degree in which the powder makeup cosmetic composition comes into close contact with the skin, the degree in which the close-contacted powder makeup cosmetic composition is sustained on the skin, and the occurrence of the crease phenomenon according to time passing.

When the hardness of the powder makeup cosmetic composition is equal to or less than 5.0 kg/cm², a thick film is formed upon skin application, so that the powder makeup cosmetic material is not fitted onto the skin or the crease phenomenon occurs, the stickiness and foreign body sensation are generated, and thus the user may feel uncomfortable. When the hardness exceeds 30 kg/cm², the amount of payoff is reduced, the expression applied to the skin is insufficient, and thus the luster of pearl and the color formation are reduced.

In addition, the powder makeup cosmetic composition of the present invention includes 40% to 70% by weight of the oil-gel phase and 30% to 60% by weight of the powder phase based on the total weight.

When the content of the oil-gel phase is less than 40% by weight based on the total weight of the powder makeup cosmetic composition, the thick feeling of use and the pay-off amount of the powder makeup cosmetic composition are increased, thereby reducing skin adhesion and deteriorating the moldability of the powder makeup cosmetic composition. Whereas, when the content of the oil-gel phase is more than 70% by weight based on the total weight of the powder makeup cosmetic composition, the relative amount of oil-gel phase is increased, thereby becoming oily and greasy and increasing the crease phenomenon.

When the content of the powder phase is less than 30% by weight based on the total weight of the powder makeup cosmetic composition, the relative amount of oil-gel phase is increased, thereby becoming oily and greasy and increasing the crease phenomenon. When the content is more than 60% by weight, the thick feeling of use and the pay-off amount are increased, thereby reducing the skin adhesion and deteriorating the moldability of the powder makeup cosmetic composition.

Further, preferably, the oil-gel phase may be 50% to 65% by weight, and the powder phase may be 35% to 50% by weight based on the total weight of the powder makeup cosmetic composition.

The oil-gel phase includes oil and a gelling agent, in which the oil is 80% to 99% by weight and the gelling agent is 1.0% to 20% by weight based on the total weight of the oil-gel phase.

Preferably, the oil may be 85% to 97% by weight, and the gelling agent may be 3.0% to 15% by weight.

The oil may use at least one selected from the group including ester-based oil including hydrogenated castor oil dimer dilinoleate, polyglyceryl-2 isostearate, polyglyceryl-2 isostearate/dimer dilinoleate copolymer, bis-ethoxydiglycol cyclohexane 1,4-dicarboxylate, pentaerythrityl tetraethylhexanoate, isodecyl neopentanoate, diisostearyl malate, caprylic/capric triglyceride, triethylhexanoin, cetyl ethylhexanoate, isotridecyl isononanoate, isopropyl myristate, isopropyl isostearate, diisopropyl dimer dilinoleate, C12-15 alkyl benzoate, isopropyl palmitate, dipropyleneglycol dibenzoate, ethylhexyl palmitate, isononyl isononanoate, neopentyl glycol diisononanoate, octyldodecyl myristate, hexyl laurate, bis-ethoxydiglycol succinate, polyglyceryl-2 diisostearate, polyglyceryl-2 diisostearate/ipdi copolymer, and isotridecyl isononanoate; silicone-based oil including cyclohexasiloxane, cyclopentasiloxane, cyclopentasiloxane/cyclohexasiloxane, phenyl trimethicone, diphenyl dimethicone, dimethicone, lauryl methicone, dimethiconol, and cetyl dimethicone; and hydrocarbon-based oil including polybutene, isohexadecane, hydrogenated polyisobutene, octyldodecanol, isododecane, squalene, mineral oil, isodecane, and hexadecene.

When the oil content is less than 85% by weight based on the total weight of the oil-gel phase, the pay-off of the powder makeup cosmetic composition does not occur, thus the skin adhesion is reduced, and the moldable temperature of the powder makeup cosmetic composition is increased, and thus the molding time is shortened, thereby lowering the moldability. In addition, when the oil content is more than 97% by weight based on the total weight of the oil-gel phase, the oil content is relatively high, thereby increasing an oily state, a greasy state and the crease phenomenon, and the hardness of the powder makeup cosmetic composition is lowered, thereby lowering the molding stability.

The gelling agent may include at least one selected from the group including starch gum-base including dextrin myristate, dextrin isostearate, dextrin palmitate, dextrin palmitate/ethylhexanoate, and maltodextrin/vp copolymer; amino acid-base including dibutyl lauroyl glutamide, and dibutyl ethylhexanoyl glutamide; polyamide-base including ethylenediamine/hydrogenated dier dilinoleate copolymer bis-di-C14-C18 alkyl amine; ammonium-base including hydroxypropyltrimonium maltodextrin crosspolymer; copolymer including dilinoleic acid/propanediol copolymer, and bis-dioctadecylamide dimer dilinoleic acid/ethylene diamine copolymer; silicon wax including bis-peg-18 methyl ether dimethyl silane, and stearyl dimethicone; synthetic wax including ethylene/propylene copolymer-synthetic wax; and hydrocarbon-based wax including 12-hydroxy stearic acid, and 10-hydroxy stearic acid, but is not limited thereto.

When the content of the gelling agent is less than 3.0% by weigh based on the total weight of the oil-gel phase, the oil content is relatively high, thus the powder makeup cosmetic composition is not applied and fitted onto the skin, and the hardness of the powder makeup cosmetic composition is lowered, thereby lowering the molding stability. In addition, when the content of the gelling agent is more than 15% by weight based on the total weight of the oil-gel phase, the pay-off of the powder makeup cosmetic composition does not occur, thereby decreasing the skin adhesion, and the moldable temperature of the powder makeup cosmetic composition is increased, and thus the molding time is shortened, thereby lowering the moldability.

The powder phase includes an inorganic pigment, an organic pigment, pearl powder and an extender pigment.

The inorganic pigment may include at least one selected from the group including red iron oxide, yellow iron oxide, black iron oxide, chromium oxide green, chromium hydroxide green, manganese violet, ultramarine, and iron oxide coating pigment.

The organic pigment may include at least one selected from the group including barium or aluminum lake pigment of yellow No. 4, yellow No. 5, red No. 201, red No. 202, red No. 218, red No. 220, red No. 226, red No. 227, blue No. 1 and blue No. 2.

The pearl powder may include at least one selected from the group including composite powder including pearl pigments, titanium oxide coated mica and titanium oxide coated calcium titanate borosilicate, bismuth oxychloride, synthetic fluorophlogite, calcium titanate borosilicate, titanium dioxide, and inorganic/organic pigments.

The extender pigment may include at least one selected from the group including muscovite mica, synthetic mica, sericite, kaolin, titanium dioxide, aluminium powder, barium sulfate, silica, zeolite, nylon, PMMA, polystyrene powder, HDI/trimethylolhexyl lactone crosspolymer-silica, dimethicone/vinyl dimethicone crosspolymer-silica, polyethylene powder, cellulose, starch powder, zinc stearate and bismuth oxychloride.

In addition to the above components, the powder makeup cosmetic composition according to the present invention may further include fragrances, preservatives, disinfectants, skin conditioners, and so on within the range not hindering the effect of the present invention.

The powder makeup cosmetic composition according to the present invention may have a formulation for a primer of base makeup, a makeup base, a foundation, a concealer, a compact powder, a lipstick, a lip gloss, an eyebrow, an eye shadow, a blusher, a highlighter, or the like, but is not limited thereto.

Hereinafter, the present invention will be described in more detail by way of Examples, Comparative Examples and Test Examples. However, the following Examples, Comparative Examples and Test Examples are provided for illustrative purposes only to understand the present invention, and the scope of the present invention is not limited by those Examples, Comparative Examples and Test Examples.

<Examples 1 to 5> Preparation Examples of Oil-Gel Phase of Powder Makeup Cosmetic Composition As shown in Table 1 below, the oil-gel phase of the powder makeup cosmetic composition was prepared by varying the components and contents.

1) The gelling agents 1 to 3 shown in the following Table 1 were mixed and heated and dissolved at 110° C. to 120° C. to prepare a mixture.

2) Oils 8 to 13 of Table 1 were mixed with the mixture of step 1), and agitated and completely dissolved using an Agi Mixer while heated at 110° C. to 120° C. to prepare an oil-gel phase.

3) The oil-gel phase of step 2) is deaerated and molded in a mold.

<Comparative Example 1> Preparation Example of Wax Solid Phase of Powder Makeup Cosmetic Composition As shown in Table 1 below, the wax solid phase of the powder makeup cosmetic composition was prepared by varying the components and contents.

1) The gelling agents 4 to 7 of Table 1 were mixed and heated and dissolved at 80° C. to 90° C. to prepare a mixture.

2) Oils 8 to 13 of Table 1 were mixed with the mixture of step 1), and agitated and completely dissolved using the Agi Mixer while heated at 80° C. to 90° C. to prepare a wax solid phase.

3) The wax solid phase of step 2) was deaerated and molded in a mold.

TABLE 1

| | | Components | Example 1 | Example 2 | Example 3 | Example 4 | Example 5 | Comparative Example 1 |
|---|---|---|---|---|---|---|---|---|
| Gelling agent | 1 | Ethylene/propylene copolymer | 1.0 | 2.0 | 3.0 | 4.0 | 6.0 | |
| | 2 | Dibutyl ethylhexanoyl glutamide | 0.8 | 3.0 | 4.0 | 5.0 | 8.0 | |
| | 3 | Maltodextrin/vpicopolymer | 0.2 | 1.0 | 1.5 | 1.8 | 3.0 | |
| | 4 | Polyethylene | | | | | | 7.0 |

TABLE 1-continued

| | Components | Example 1 | Example 2 | Example 3 | Example 4 | Example 5 | Comparative Example 1 |
|---|---|---|---|---|---|---|---|
| Oil | 5 Ozokerite | | | | | | 4.0 |
| | 6 Paraffin | | | | | | 1.0 |
| | 7 Beads wax | | | | | | 7.0 |
| | 8 Isododecane | 5.0 | 5.0 | 5.0 | 5.0 | 5.0 | 5.0 |
| | 9 Polybutene | 10.0 | 10.0 | 10.0 | 10.0 | 10.0 | 10.0 |
| | 10 Diisostearyl malate | 10.0 | 10.0 | 10.0 | 10.0 | 10.0 | 10.0 |
| | 11 Neopentyl glycol diethyl hexanoate | 15.0 | 15.0 | 15.0 | 15.0 | 15.0 | 15.0 |
| | 12 Polyglyceryl-2 triisostearate | 10.0 | 10.0 | 10.0 | 10.0 | 10.0 | 10.0 |
| | 13 Triethylhexanoin | 48.0 | 44.0 | 41.5 | 39.2 | 33.0 | 31.0 |
| | Sum | 100 | 100 | 100 | 100 | 100 | 100 |

<Test Example 1> Measurement on Hardness of Oil-Gel Phase and Wax Solid Phase

The hardness of the oil-gel phase and the wax solid phase prepared in Examples 1 to 5 and Comparative Example 1 was measured. The hardness was measured using a Rheometer (Sun Scientific Inc. an adapter pin (ϕ 3 mm)), and the measurement was performed five times to obtain an average value, and the results are shown in Table 2 below.

TABLE 2

| | Example 1 | Example 2 | Example 3 | Example 4 | Example 5 | Comparative Example 1 |
|---|---|---|---|---|---|---|
| Hardness (kg/cm$^2$) | 3.0 | 8.0 | 14.0 | 19.0 | 36.0 | 18.0 |

As shown in Table 2, the hardness of Example 1 was 3.0 kg/cm$^2$, which was the softest phase among the examples and comparative example.

The hardness of Examples 2 to 4 was 8.0 kg/cm$^2$ to 19.0 kg/cm$^2$, and the hardness of Example 5 was 36.0 kg/cm$^2$, which was the hardest phase among the examples and comparative example.

The hardness of Comparative Example 1 was 18.0 kg/cm$^2$ and prepared to have the hardness similar to Examples 3 and 4.

Accordingly, in Example 1, since the hardness is low, it was difficult to maintain a shape after molding due to easy breakage, and it was unsuitable for molding the composition into a three-dimensional shape. In Example 5, since the hardness was high, the shape was maintained after molding, but there was no pay-off.

<Examples 6 to 9> Preparation Example of Powder Makeup Cosmetic Composition

As shown in Table 3 below, the powder makeup cosmetic composition was prepared by mixing powders 6 to 10 of Table 3 with the oil-gel phases of Examples 2 to 5.

1) The oil-gel phases of Examples 2 to 5 were heated and dissolved at 80° C. to 100° C.
2) Powders 6 to 10 of Table 3 were mixed to form a powder phase.
3) While the dissolved oil-gel phase of step 1) was heated to 80° C. to 100° C. and agitated with the Agi Mixer, the powder phase of step 2) was slowly added and mixed to prepare a powder makeup cosmetic composition.
4) The powder makeup cosmetic composition of step 3) was deaerated while the temperature of step 3) being maintained, and molded in the mold.

<Comparative Example 2> as Shown in Table 3 Below, the Powder Makeup Cosmetic Composition was Prepared by Mixing Powders 6 to 10 of Table 3 with the Wax Solid Phase of Comparative Example 1

1) The wax solid phase of Comparative Example 1 was heated and dissolved at 80° C. to 90° C.
2) Powders 6 to 10 of Table 3 were mixed to form a powder phase.
3) While the dissolved wax solid phase of step 1) was heated to 80° C. to 90° C. and agitated with the Agi Mixer, the powder phase of step 2) was slowly added and mixed to prepare a powder makeup cosmetic composition.
4) The powder makeup cosmetic composition of step 3) was deaerated while the temperature of step 3) being maintained, and molded in the mold.

TABLE 3

| Components | Example 6 | Example 7 | Example 8 | Example 9 | Comparative Example 2 |
|---|---|---|---|---|---|
| 1 Oil-gel phase of Example 2 | 60.0 | | | | |
| 2 Oil-gel phase of Example 3 | | 60.0 | | | |
| 3 Oil-gel phase of Example 4 | | | 60.0 | | |
| 4 Oil-gel phase of Example 5 | | | | 60.0 | |

TABLE 3-continued

| | | Components | Example 6 | Example 7 | Example 8 | Example 9 | Comparative Example 2 |
|---|---|---|---|---|---|---|---|
| | 5 | Wax solid phase of Comparative Example 1 | | | | | 60.0 |
| Powder | 6 | Methyl methacrylate crosspolymer | 2.0 | 2.0 | 2.0 | 2.0 | 2.0 |
| | 7 | Silica | 2.0 | 2.0 | 2.0 | 2.0 | 2.0 |
| | 8 | Black iron oxide/mica/titanium dioxide | 6.0 | 6.0 | 6.0 | 6.0 | 6.0 |
| | 9 | Calcium titanium borosilicate/titanium dioxide/tin oxide | 10.0 | 10.0 | 10.0 | 0.0 | 10.0 |
| | 10 | Mica/Ferrous oxide | 20.0 | 20.0 | 20.0 | 20.0 | 20.0 |
| | | Sum | 100 | 100 | 100 | 100 | 100 |

<Test Example 2> Evaluation on Molding Stability

The molding stability was evaluated with respect to the powder makeup cosmetic compositions of Examples 6 to 9 and Comparative Example 2 by measuring the hardness, dropping stability and high-temperature stability.

The hardness was measured using a Rheometer (Sun Scientific Inc. an adapter pin ($\phi$ 3 mm)), the measurement was performed five times to obtain an average value, and the results are shown in Table 4 below.

As for the Dropping stability, after the powder makeup cosmetic compositions of Examples 6 to 9 and Comparative Example 2 were placed in a container, a free fall was made with respect to a front, back, and side thereof onto the rubber plate having 5 mm thickness from a height of 70 cm.

The evaluation was repeated 10 times and the results are shown in Table 4 below.

As for the high-temperature stability, the makeup cosmetic compositions of Examples 6 to 9 and Comparative Example 2 were placed at a temperature of 45° C. for three weeks, and a separation state was observed as time passed. The results are shown in Table 4 below.

TABLE 4

| | Example 6 | Example 7 | Example 8 | Example 9 | Comparative Example 2 |
|---|---|---|---|---|---|
| Hardness (kg/cm²) | 6.0 | 12.0 | 16.0 | 33.0 | 10.0 |
| Dropping stability | X | X | X | X | Δ |
| High-temperature stability | Δ | X | X | X | Δ |

Evaluation criteria of the dropping stability: Stable (X), Fine cracks or deflection (Δ), Complete breakage (○)
Evaluation criteria of the high-temperature stability: Stable (X), Slightly separated (Δ), Completely separated (○)

As shown in Table 2, the difference between the hardnesses of Examples 6 to 9 and the hardnesses of Examples 2 to 5 containing Examples 6 to 9 was 2 kg/cm² to 3 kg/cm², and the difference between the hardness of Comparative Example 2 and Comparative Example 1 was 8 kg/cm².

In addition, Comparative Example 2 had the hardness closest to that of Example 7.

In other words, it was found that, when the wax solid phase of Comparative Example 1 was mixed with a predetermined amount of powder phase to prepare a powder makeup cosmetic composition, the hardness was remarkably lowered, and it was found that even when the oil-gel phases of Examples 2 to 5 was mixed with a certain amount of the powder phase to prepare a powder makeup cosmetic composition, the powder makeup cosmetic composition was stable even after molding because the change in hardness was small.

As a result of observing the dropping stability of Examples 6 to 9 and Comparative Example 2, Examples 6 to 9 were stable after the dropping without breakage or deflection of the powder makeup cosmetic composition, and the powder makeup cosmetic composition of Comparative Example 2 was slightly deflected in one direction.

When Example 7 is compared with Comparative Example 2, in Example 7, the powder makeup cosmetic composition was prepared by containing a powder phase in an oil-gel phase. In Comparative Example 2, the powder makeup cosmetic composition was prepared by containing the powder phase in the oil-gel phase. Although the hardness of Example 7 had a slight difference with respect to the hardness of Comparative Example 2, Example 7 was stable in the drop stability, but Comparative Example 2 was deflected in one direction.

In other words, in Example 7, it was found that the powder makeup cosmetic composition maintained the drop stability even after molding because the oil gel phase was contained.

As for the high-temperature stability, Example 6 and Comparative Example 2 had a slight separation and thus oil was formed on a surface of the powder makeup cosmetic composition. However, when returning to an original state after stored at room temperature, the oil was not observed on the surface of the powder makeup cosmetic composition.

The powder makeup cosmetic compositions of Examples 7 to 9 had no separation.

<Test Example 3> Evaluation on Moldability

In order to evaluate the molding temperature and the moldability with respect to the powder makeup cosmetic compositions of Examples 6 to 9 and Comparative Example 2, each powder makeup cosmetic composition was molded into a design rubber at a predetermined temperature, and cooled at a temperature of 5° C. for 5 minutes and released from the mold.

The molding temperature was estimated by measuring the temperature at which the powder makeup cosmetic composition was most clearly molded into a shape of the design rubber, and the moldability was evaluated by the degree to which the shape of the design rubber was clearly formed in the powder makeup cosmetic composition.

When the grade was low, the moldability was estimated as difficult to delicately design, and the results are shown in Table 5 below.

TABLE 5

|  | Example 6 | Example 7 | Example 8 | Example 9 | Comparative Example 2 |
|---|---|---|---|---|---|
| Molding temperature (° C.) | 65 to 75 | 75 to 85 | 85 to 95 | 95 to 110 | 80 to 85 |
| Moldability | 4 | 5 | 5 | 3 | 4 |

Evaluation criteria of the moldability: Very good (5), Good (4), Normal (3), Bad (2), Very bad (1)

Comparing the molding temperatures between Examples 6 to 9 and Comparative Example 2, the molding temperature was lowest in Example 6 at 65° C., to 75° C., and highest in Example 9 at 95° C. to 110° C. Whereas, the moldability of Example 9 was the lowest, and the moldabilities of Examples 7 and 8 were excellent.

Since Example 6 had a low molding temperature, the temperature may be easily adjusted, but may have a low moldability compared with Examples 7 to 8. Since Example 9 had a high molding temperature, the temperature may be difficult to adjust, and since the moldability was low, it was difficult to obtain a desired three-dimensional shape.

In addition, since the design rubber was damaged by heat, the rubber was easily deformed. In addition, Examples 7 and showed the best moldability, and had a higher molding temperature compared to Example 6. However, since the molding temperature did not exert an impact on the design rubber, the three-dimensional shape to be formed was obtained.

Accordingly, it was found that Examples 7 and 8 among Examples 6 and 9 had suitable molding temperatures, had good moldabilities, and the molded object was preferably molded.

<Test Example 4> Evaluation of the Effectiveness of Use

The soft feeling of use, spreadability, adhesion, sustain power, and generation of creases were evaluated with respect to the powder makeup cosmetic compositions of Examples 6 to 9 and Comparative Example 2. For the evaluation, twenty women using eye shadows were tested as subjects to use the eye shadows for a week, and then the sensory evaluation was performed on the feeling and state during use.

The soft feeling of use was evaluated by the spreadability and stickiness upon application. The sustain power was evaluated by comparing the degree of color formation immediately after the application with the degree of color formation after 6 hours. The crease occurrence was evaluated by comparing the degree of crease immediately after the application with the degree of crease after 6 hours.

TABLE 6

| Evaluation items | Example 6 | Example 7 | Example 8 | Example 9 | Comparative Example 2 |
|---|---|---|---|---|---|
| Soft feeling of use | 5 | 5 | 5 | 3 | 3 |
| Spreadability | 4 | 5 | 5 | 3 | 3 |
| Adhesion upon application | 5 | 5 | 5 | 4 | 4 |
| Durability | 5 | 5 | 5 | 5 | 3 |
| Crease occurrence | 4 | 5 | 5 | 5 | 2 |

Evaluation criteria: Very good (5), Good (4), Normal (3), Bad (2), Very bad (1)

As shown in Table 6, the result showed that Examples 7 and 8 were the best in all evaluation items, and Comparative Example 2 was the worst.

Comparing Examples 6 to 9, it was found that Examples 6 to 8 were excellent in soft feeling of use, adhesion and durability upon the application, and the adhesion and spreadability in Example 9 were deteriorated upon the application because the pay-off amount was decreased due to the high hardness.

In addition, Comparing Examples 6 and 9, Example 6 had the excellent soft feeling of use due to the low hardness, but there was a high possibility of the creases due to an increase of the pay-off amount. In Example 9, because the pay-off amount was reduced due to the high hardness, there was a low possibility of the creases, but the soft feeling of use was lowered.

Comparing Comparative Example 2 with Example 7, it was found that Example 7 was superior to Comparative Example 2 in the soft feeling of use and the spreadability. In other words, it is interpreted that the powder makeup cosmetic composition had the stickiness and the poor spreadability due to the wax solid phase of Comparative Example 2, the soft feeling of use was insufficient, and the possibility of the creases is high as time passes.

The invention claimed is:

1. A three-dimensional molding powder makeup cosmetic composition containing a powder phase in an oil-gel phase, the three-dimensional molding powder makeup cosmetic composition comprising:
   40 wt % to 70 wt % of the oil-gel phase, and 30 wt % to 60 wt % of the powder phase,
   wherein the oil-gel phase includes 85 wt % to 97 wt % of oil and 3 wt % to 15 wt % of a gelling agent,
   wherein the oil includes isododecane, polybutene, diisostearyl malate, neopentyl glycol diethylhexanoate, polyglyceryl-2 triisostearate, and triethylhexanoin,
   wherein the gelling agent includes an ethylene/propylene copolymer, dibutyl ethylhexanoyl glutamide, and maltodextrin/VP copolymer,
   wherein the powder phase includes methyl methacrylate crosspolymer, silica, black iron oxide/mica/titanium dioxide, calcium titanium borosilicate/titanium dioxide/tin oxide, and mica/ferrous oxide,
   wherein the powder makeup cosmetic composition has a hardness in a range of 5.0 kg/cm$^2$ to 30 kg/cm$^2$, and
   wherein the powder makeup cosmetic composition is molded by a design rubber at a molding temperature of 75° C. to 100° C., cooled at 5° C. for five minutes, and released.

2. The three-dimensional molding powder makeup cosmetic composition of claim 1, wherein the molding temperature of the powder makeup cosmetic composition is in a range of 75° C. to 95° C.

* * * * *